(12) United States Patent
Prawel

(10) Patent No.: US 11,957,572 B2
(45) Date of Patent: Apr. 16, 2024

(54) SYSTEMS AND METHODS FOR MANUFACTURING CUSTOMIZED MEDICAL DEVICES

(71) Applicant: Colorado State University Research Foundation, Fort Collins, CO (US)

(72) Inventor: David Prawel, Loveland, CO (US)

(73) Assignee: COLORADO STATE UNIVERSITY RESEARCH FOUNDATION, Fort Collins, CO (US)

( * ) Notice: Subject to any disclaimer, the term of this patent is extended or adjusted under 35 U.S.C. 154(b) by 795 days.

(21) Appl. No.: 16/475,153

(22) PCT Filed: Jan. 30, 2018

(86) PCT No.: PCT/US2018/015967
§ 371 (c)(1),
(2) Date: Jul. 1, 2019

(87) PCT Pub. No.: WO2018/144462
PCT Pub. Date: Aug. 9, 2018

(65) Prior Publication Data
US 2019/0328517 A1    Oct. 31, 2019

Related U.S. Application Data

(60) Provisional application No. 62/453,918, filed on Feb. 2, 2017.

(51) Int. Cl.
*B33Y 10/00* (2015.01)
*A61B 34/10* (2016.01)
(Continued)

(52) U.S. Cl.
CPC ............ *A61F 2/2415* (2013.01); *A61B 34/10* (2016.02); *A61F 2/07* (2013.01); *A61F 2/90* (2013.01);
(Continued)

(58) Field of Classification Search
CPC .. A61F 2/2415; A61F 2/07; A61F 2/90; A61F 2210/0071; A61F 2240/004;
(Continued)

(56) References Cited

U.S. PATENT DOCUMENTS 6,171,335 B1 *   1/2001   Wheatley .............. A61F 2/2412
                                                     623/2.12
2008/0058633 A1   3/2008   Boyden et al.
(Continued)

FOREIGN PATENT DOCUMENTS

WO    WO 2016/115369 A1    7/2016

OTHER PUBLICATIONS

Duan B et al. 3D Bioprinting of heterogeneous aortic valve conduits with alginate/gelatin hydrogels. Journal of Biomedical Materials Research A. Month 2012 vol. 00A, Issue 00.
(Continued)

*Primary Examiner* — Yung-Sheng M Tsui
*Assistant Examiner* — Melody Tsui
(74) *Attorney, Agent, or Firm* — Polsinelli PC

(57) ABSTRACT

Implementations described and claimed herein provide systems and methods for manufacturing customized cardiovascular devices. In one implementation, patient cardiovascular data for a patient is received at a controller. The patient cardiovascular data is captured using a patient interface. A printing profile for a cardiovascular medical device is received at the controller. A patient specific three-dimensional model of the cardiovascular medical device customized for the patient using the patient cardiovascular data and the printing profile is generated. The patient specific three-dimensional model of the cardiovascular medical device is sliced into a plurality of outlines using the controller. Print instructions based on the plurality of outlines are generated using the controller. A polymeric material is manipulated
(Continued)

according to the print instructions into a customized polymeric cardiovascular medical device for the patient. The customized polymeric cardiovascular medical device includes at least one micro-geometry.

22 Claims, 11 Drawing Sheets

(51) Int. Cl.
| | |
|---|---|
| A61F 2/07 | (2013.01) |
| A61F 2/24 | (2006.01) |
| A61F 2/90 | (2013.01) |
| A61L 27/18 | (2006.01) |
| B29C 64/153 | (2017.01) |
| B29C 64/393 | (2017.01) |
| B33Y 30/00 | (2015.01) |
| B33Y 80/00 | (2015.01) |

(52) U.S. Cl.
CPC ............ *A61L 27/18* (2013.01); *B29C 64/153* (2017.08); *B29C 64/393* (2017.08); *B33Y 10/00* (2014.12); *B33Y 30/00* (2014.12); *B33Y 80/00* (2014.12); *A61B 2034/108* (2016.02); *A61F 2210/0071* (2013.01); *A61F 2240/004* (2013.01); *A61L 2430/20* (2013.01)

(58) Field of Classification Search
CPC ......... B33Y 10/00; B33Y 30/00; B33Y 80/00; A61B 34/10; A61B 2034/108; B29C 64/153; B29C 64/393; A61L 27/18; A61L 2430/20
See application file for complete search history.

(56) References Cited

U.S. PATENT DOCUMENTS

| | | | |
|---|---|---|---|
| 2014/0309523 A1 | 10/2014 | Daon et al. | |
| 2015/0320956 A1* | 11/2015 | Dunne | B29C 33/52 128/207.14 |
| 2016/0303804 A1* | 10/2016 | Grbic | G06T 19/00 |
| 2017/0360578 A1* | 12/2017 | Shin | G09B 23/286 |
| 2023/0119492 A1* | 4/2023 | Angelini | B29C 64/40 264/494 |

OTHER PUBLICATIONS

International Search Report and Written Opinion, PCT/US2018/015967, dated Apr. 13, 2018.

Witschey WRT et al. Three-Dimensional Ultrasound-Derived Physical Mitral Valve Modeling. Annals of Thoracic Surgery 2014;98:691-4.

* cited by examiner

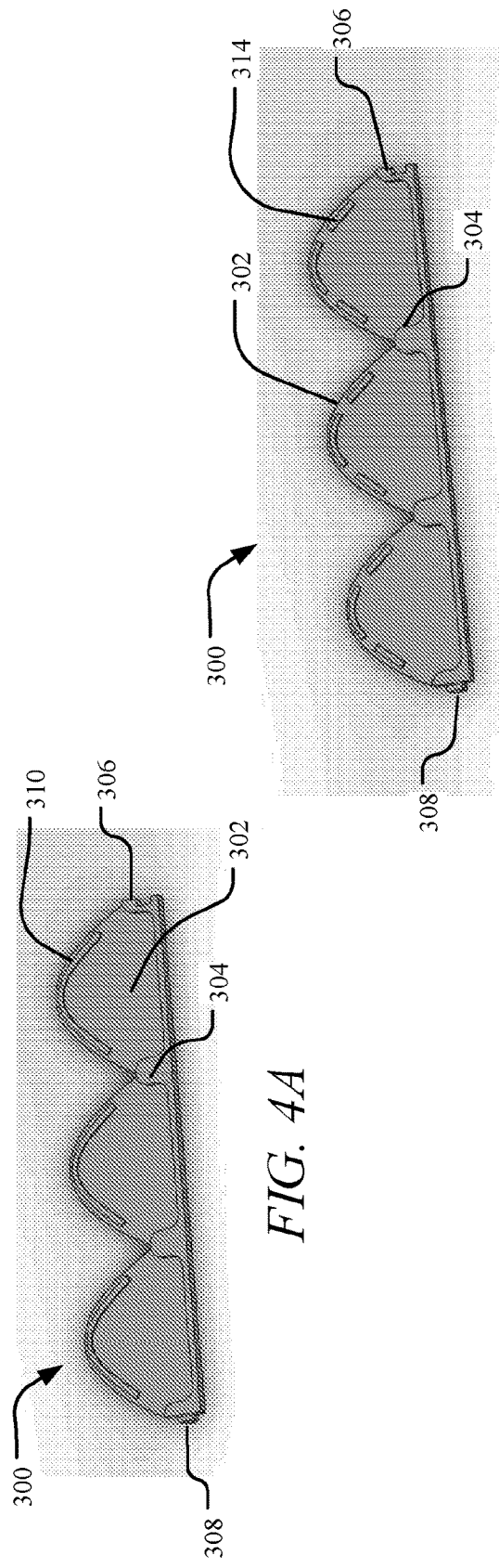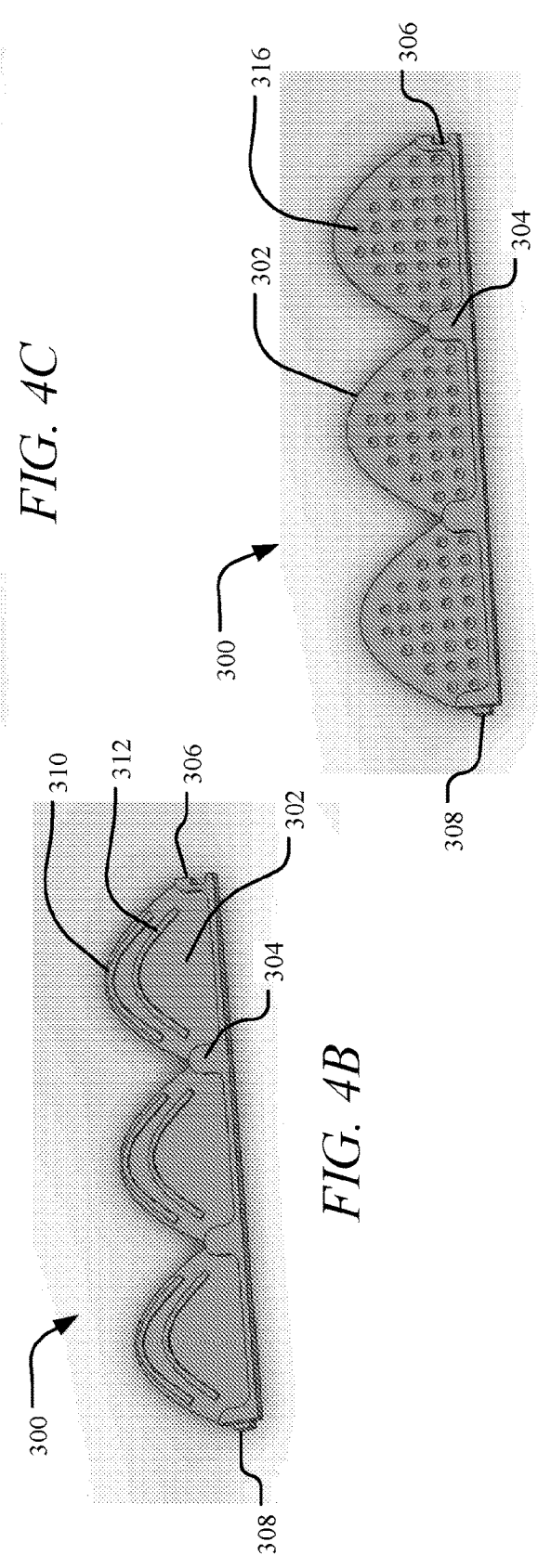

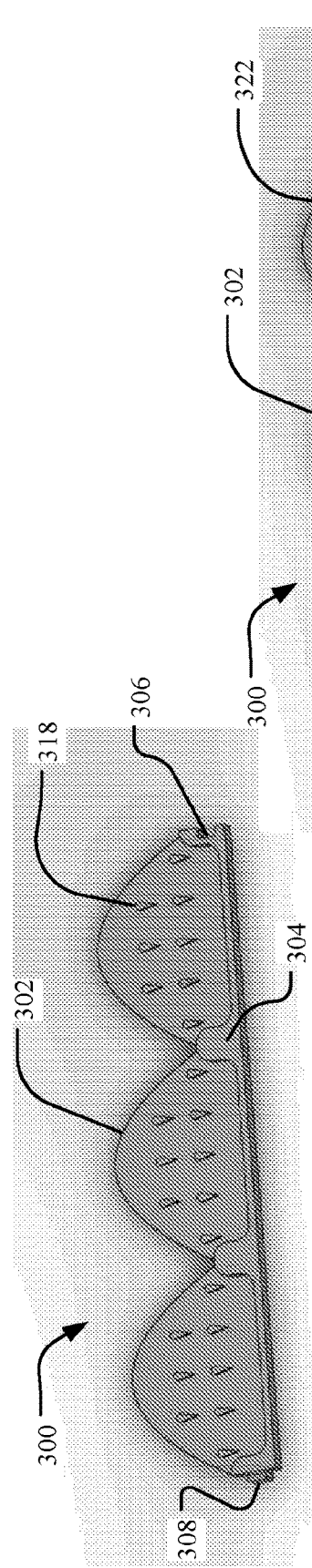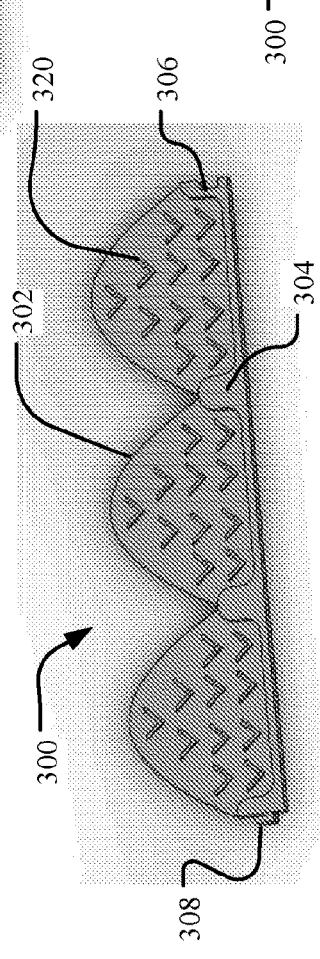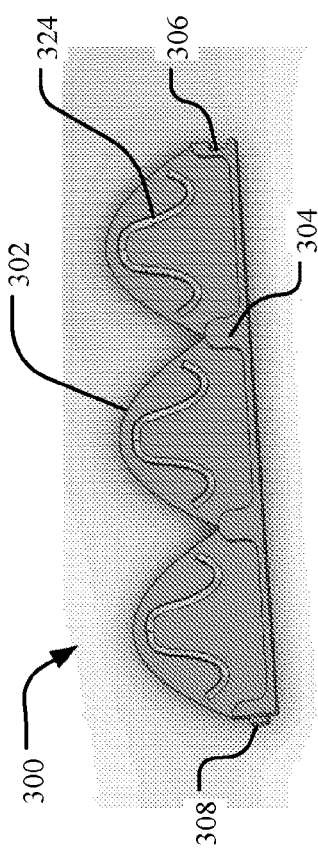

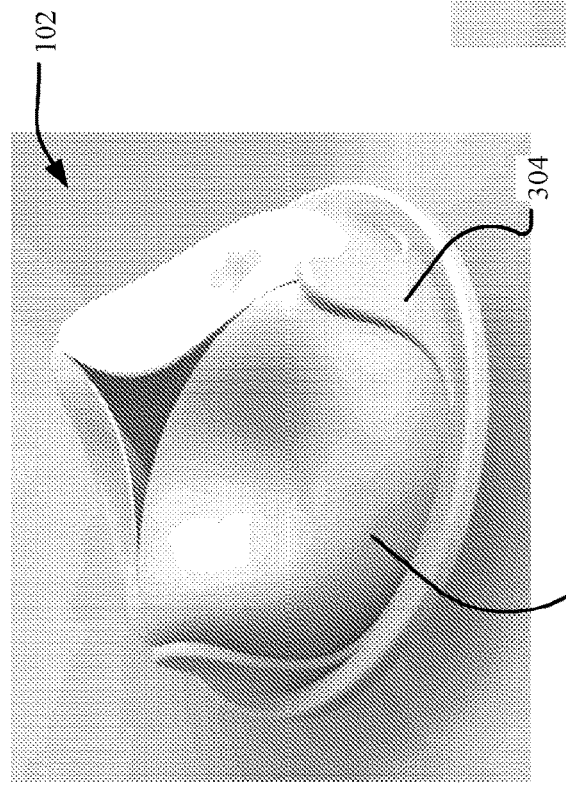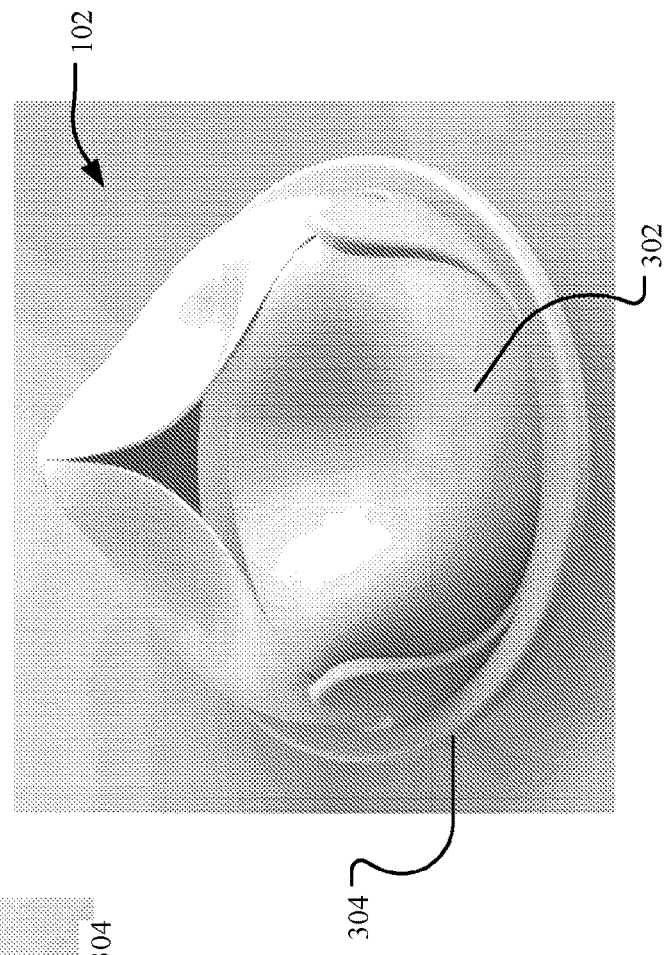
FIG. 6A
FIG. 6B

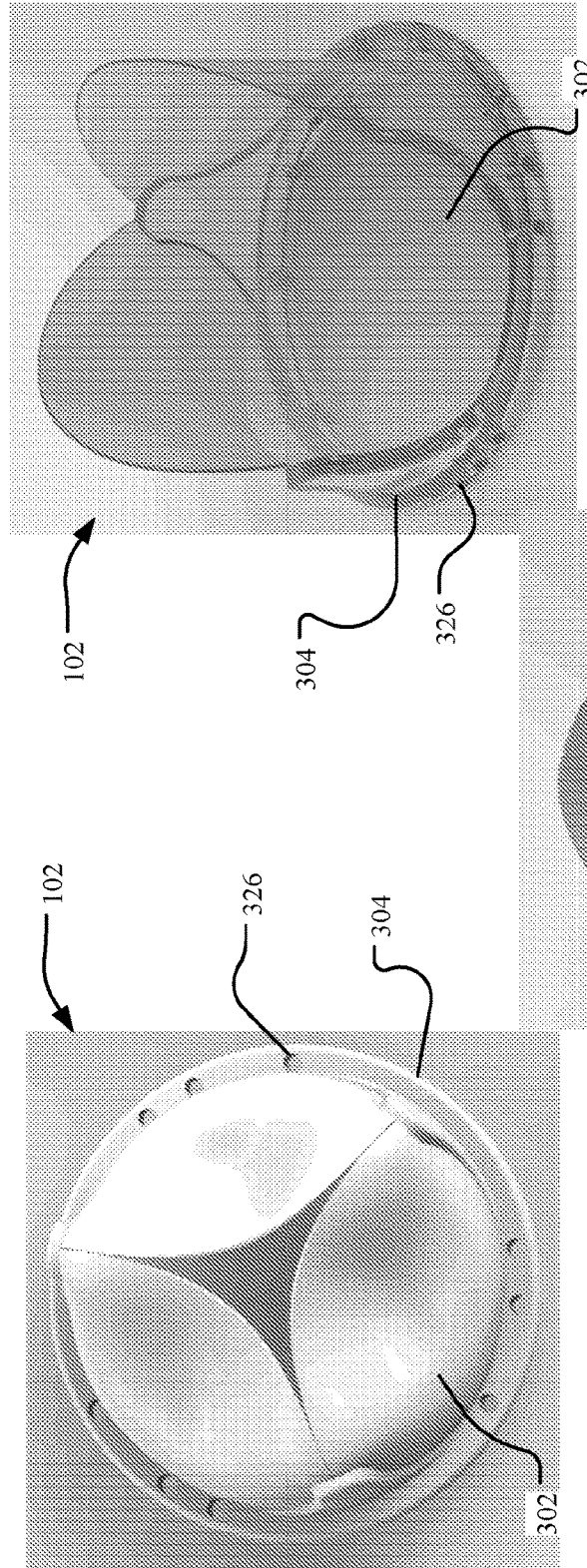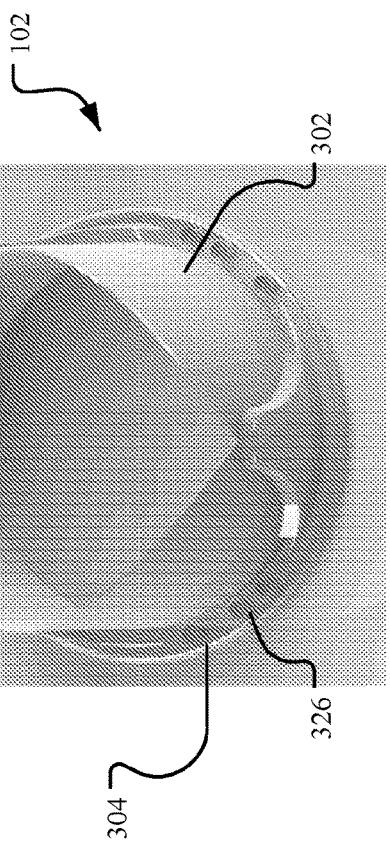
FIG. 8A
FIG. 8B
FIG. 8C

SYSTEMS AND METHODS FOR MANUFACTURING CUSTOMIZED MEDICAL DEVICES

CROSS-REFERENCE TO RELATED APPLICATIONS

The present application claims priority to U.S. Provisional Patent Application No. 62/453,918, which was filed on Feb. 2, 2018, and is entitled Systems and Methods for Manufacturing Customized Medical Devices. The content of the above-mentioned patent application is hereby incorporated by reference in its entirety.

TECHNICAL FIELD

Aspects of the present disclosure relate to the manufacture of customized polymeric medical devices, and in particular, systems and methods for manufacturing thin-walled cardiovascular medical devices with a customized profile and/or micro-geometry using thermoplastic elastomeric materials.

BACKGROUND

Heart disease remains a leading cause of death in the United States and globally, with people of all ages and backgrounds being susceptible to the condition in various forms. Cardiovascular devices may be surgically implanted in a patient to repair, replace, or otherwise provide therapy for damaged cardiovascular anatomy. For example, patients suffering from aortic stenosis or similar heart valve diseases may undergo surgery to replace a defective heart valve with a prosthetic valve. As another example, a stent may be placed in a narrow or blocked artery during a percutaneous coronary intervention to restore blood flow. Such cardiovascular devices are typically challenging to manufacture. Due to manufacturing constraints, many conventional cardiovascular devices are difficult to fit within the patient anatomical structures during a surgical procedure and/or are prone to reduced operability to provide effective therapy within the environment of the patient anatomy. Further, these conventional cardiovascular devices fail to account for patient-specific morphologies and particular surgical approaches.

It is with these observations in mind, among others, that various aspects of the present disclosure were conceived and developed.

SUMMARY

Implementations described and claimed herein address the foregoing problems by providing systems and methods for manufacturing customized cardiovascular devices. In one implementation, patient cardiovascular data for a patient is received at a controller. The patient cardiovascular data is captured using a patient interface. A printing profile for a cardiovascular medical device is received at the controller. A patient specific three-dimensional model of the cardiovascular medical device customized for the patient using the patient cardiovascular data and the printing profile is generated. The patient specific three-dimensional model of the cardiovascular medical device is sliced into a plurality of outlines using the controller. Print instructions based on the plurality of outlines are generated using the controller. A polymeric material is manipulated according to the print instructions into a customized polymeric cardiovascular medical device for the patient. The customized polymeric cardiovascular medical device includes at least one micro-geometry.

Other implementations are also described and recited herein. Further, while multiple implementations are disclosed, still other implementations of the presently disclosed technology will become apparent to those skilled in the art from the following detailed description, which shows and describes illustrative implementations of the presently disclosed technology. As will be realized, the presently disclosed technology is capable of modifications in various aspects, all without departing from the spirit and scope of the presently disclosed technology. Accordingly, the drawings and detailed description are to be regarded as illustrative in nature and not limiting.

BRIEF DESCRIPTION OF THE DRAWINGS

FIGS. 4A-4D show the heart valve leaflet sheet with various examples of customized flow manager geometries.

FIGS. 5A-5D show the heart valve leaflet sheet with additional examples of customized flow manager geometries.

FIGS. 6A-6B illustrate perspective views of an example customized polymeric cardiovascular device in the form of a heart valve shown with the leaflets folded.

FIG. 8A illustrates a top view of an example heart valve shown with the leaflets folded and including customized suture holes defined in the annulus.

FIGS. 8B and 8C are perspective views of the heart valve of FIG. 8A shown with the leaflets displaced.

DETAILED DESCRIPTION

Aspects of the present disclosure involve systems and methods for manufacturing customized polymeric cardiovascular medical devices. Generally, a cardiovascular medical device is customized for a patient and printed with one or more layers of polymeric material, including, thermoplastic elastomeric (TPE) materials, such as thermoplastic (poly)urethane (TPU), photopolymers, and/or the like, using a three-dimensional (3D) printer. In one aspect, the cardiovascular medical device is customized for the patient using a patient-specific 3D model generated using patient cardiovascular data and/or a printing profile. The patient-specific 3D model is sliced into several cross-sections from which print instructions are generated. The print instructions define the actions of the 3D printer as the customized polymeric cardiovascular medical device is manufactured. The customized polymeric cardiovascular medical device may include one or more micro-geometries, profiles, shapes, sizes, and/or other features customized for the patient, the physician performing the procedure, and/or the procedure. The customized cardiovascular devices thus have an optimized performance both in the context of the integrity and functionality of the device individually as well as in the context of the biological functionality of the device working in conjunction with the anatomy of the patient. The overall geometry, including the profile, shape, size, and micro-geometries, in combination with the optimized performance create a patient-specific customized medical device.

The presently disclosed technology is described herein with respect to cardiovascular medical devices, such as heart valves, surrogate blood vessels (e.g., vascular grafts), embolism repair sleeves, catheters, gaskets, stents, and other cardiovascular devices, surrogate tissues, and/or biomaterial formulations. However, it will be appreciated that the presently disclosed technology may extend to other devices within and outside of the cardiovascular medical context, such as hernia mesh. More particularly, medical devices, surrogate tissues, and other biomaterial formulations customized for the target anatomy of a patient may be printed as thin sheets of TPE or other thermofusible biocompatible material or as structures with various morphologies. Other materials may also be chemically or locally modified to form a customized elastomer for a particular type of medical device. Thus, the presently disclosed technology generally provides for systems and methods for manufacturing customized polymeric medical devices customized for a patient.

Figure 1:
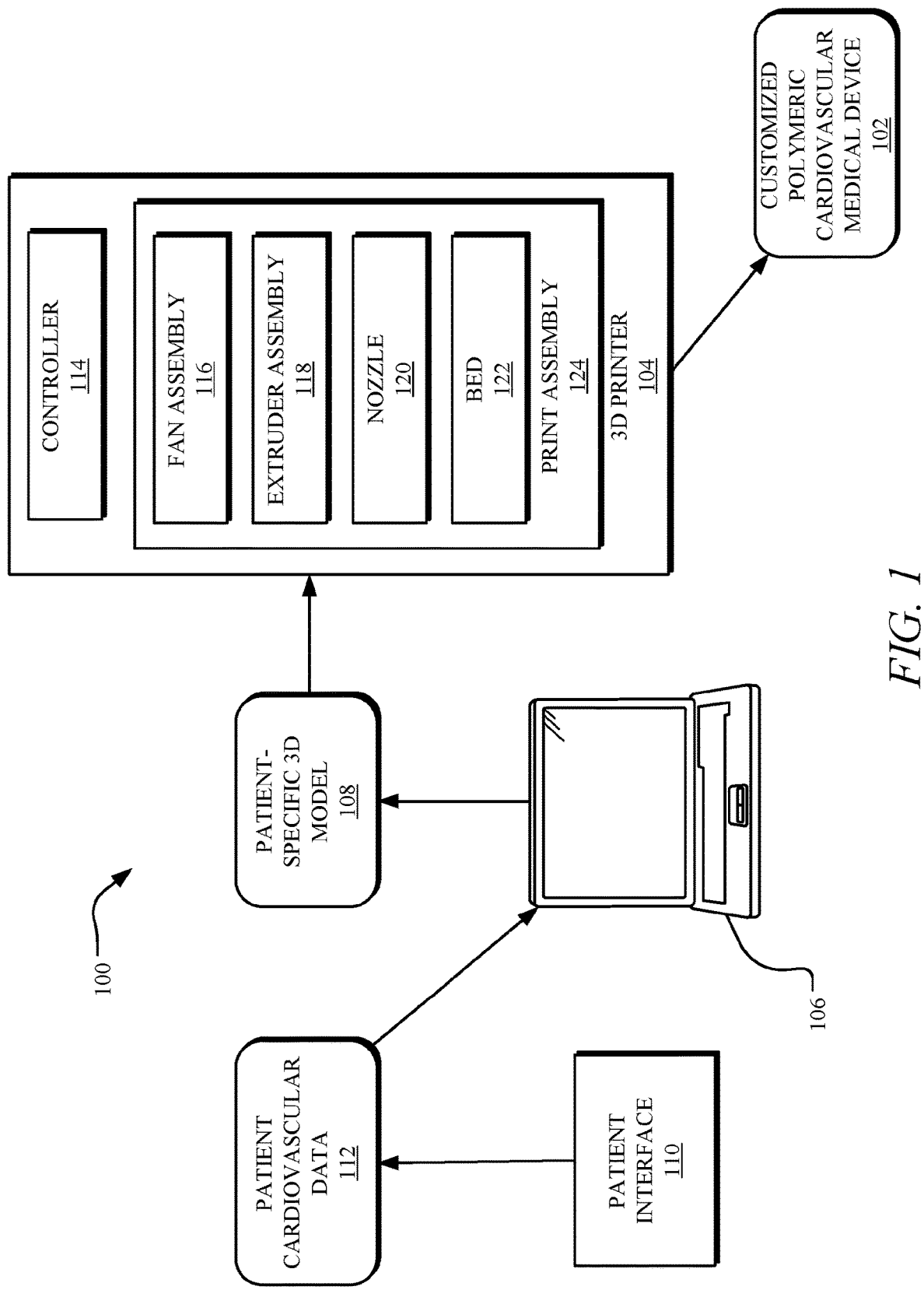
FIG. 1 is a block diagram of an example system for manufacturing customized polymeric cardiovascular devices.

To begin a detailed description of an example system 100 for manufacturing a customized polymeric cardiovascular medical device 102 for a patient using a 3D printer 104, reference is made to FIG. 1. In one implementation, the customized polymeric cardiovascular medical device 102 is manufactured based on a patient-specific 3D model 108. The patient-specific 3D model 108 may be generated using the 3D printer 104 or a user device 106.

The user device 106 is generally any form of computing device capable of interacting with the 3D printer 104, such as a personal computer, terminal, workstation, mobile device, cell phone, tablet, or the like. The user device 106 may be in communication with the 3D printer 104 via a wired (e.g., Universal Serial Bus, Ethernet, etc.) or wireless connection (e.g., WiFi, Bluetooth, etc.). For example, the 3D printer 104 may include a network interface for facilitating communication with the user device 106 via a network. In another implementation, the patient-specific 3D model 108 is received at the 3D printer 104 from the user device 106 via removable memory, such as a flash drive.

In one implementation, the patient-specific 3D model 108 is customized for the patient using patient cardiovascular data 112, including information regarding the patient anatomy and physiology. For example, the patient cardiovascular data 112 may include, without limitation, information regarding patient blood flow, heart rhythm, anatomy structure, and/or other aspects about the health of the patient heart and/or circulation system, including any patient specific morphologies. The patient cardiovascular data 112 may be captured using a patient interface 110, which communicates the patient cardiovascular data 112 to the user device 106 or the 3D printer 104 via a wired or wireless connection. The patient interface 110 may include, without limitation, at least one probe, electrocardiograph, ultrasound device, computed tomography device, magnetic resonance imaging device, and/or other devices for measuring or capturing the patient cardiovascular data 112. The patient interface 110 may include a probe in the form of a transducer adapted to alternate between sending and receiving signals. For example, the probe may be an ultrasonic transducer adapted to intermittently or continuously produce and detect ultrasonic waves. However, the patient interface 110 may include a probe with pressure, flow, impedance, conduction, electrical, and/or temperature sensors in lieu of or in addition to ultrasonic transducers.

Using the patient cardiovascular data 112, the patient-specific 3D model 108 is customized for the target anatomy of the patient, including any patient-specific morphologies. The patient-specific 3D model 108 may be further customized to incorporate physician preferences and/or accommodate any particularities of the procedure to implant or otherwise deploy the customized polymeric cardiovascular medical device 102. For example, one or more micro-geometries, device profiles, shapes, thicknesses, flexibility, sizes, and/or other features of the customized polymeric cardiovascular medical device 102 may be customized in the patient-specific 3D model 108.

In one implementation, various features of the patient-specific 3D model 108 are customized in the patient-specific 3D model 108 using a print profile. The user device 106 may capture the print profile and communicate it to the 3D printer 104, or the print profile may be captured using an interface of the 3D printer 104. In one implementation, the print profile includes, but is not limited to, a filament diameter, a temperature, a printing speed, a layer height, a coasting distance, and/or other printing parameters selected for the customized polymeric cardiovascular medical device 102. It will be appreciated that the print profile may be selected or modified based on a material selection and a printing environment. For example, the 3D printer 104 may print the customized polymeric cardiovascular medical device 102 through melt extrusion, photopolymerization, sintering, fused filament fabrication, and/or the like. The print profile thus include printing parameters selected for printing the customized polymeric cardiovascular medical device 102 in a particular printing environment.

The patient-specific 3D model 108 is a representation of the customized polymeric cardiovascular medical device 102, including small details and features customized for the patient. The patient-specific 3D model 108 is sliced into a plurality of outlines, such as a series of sequential cross-sections of the patient-specific 3D model 108. The plurality of outlines is used to produce print instructions for the customized polymeric cardiovascular medical device 102. The print instructions may be in a format including, but not limited to, GCODE, STL, and/or other formats ingestible by the 3D printer 104. The print instructions define the actions of one or more components of the 3D printer 104 during manufacturing of the customized polymeric cardiovascular medical device 102.

The 3D printer 104 includes a controller 114 configured to direct the actions of the one or more components of a print assembly 124 of the 3D printer 104 according to the print instructions. In one implementation, the print assembly 124 manufactures the customized polymeric cardiovascular medical device 102 using an additive process in which the material is deposited layer by layer. For example, the print assembly 124 may perform filament fabrication using a controlled extrusion of molten thermoplastic feedstock. The print assembly 124 may alternatively use light to cure a photopolymer and/or a selective laser sintering process to fuse powdered metal, such as biocompatible metal, together.

In one implementation, the print assembly 124 includes a fan assembly 116, an extruder assembly 118, at least one nozzle 120, and a bed 122, each controlled by the controller 114. It will be appreciated that the 3D printer 104 may include additional, fewer, or different components.

The bed 122 may be a platform disposed distally and vertically translatable relative to the nozzle 120. Stated differently, the bed 122 is positioned under the nozzle 120 at a distance that may be adjusted, for example, as the 3D printer 104 manufactures the customized polymeric cardiovascular medical device 102. Prior to depositing the first layer, the bed 122 is wiped clean of debris, wiped with acetone or similar composition, and a glass surface left untreated. In one particular example implementation, the bed 122 is a heated borosilicate glass bed, and the extruder assembly 118 is a dual-material extruder assembly, equipped with a heater.

The extruder assembly 118 may include an extrusion head that receives and heats a stream of filament material, such as TPE material. In one example, the primary extruder is a TPU extruder. The temperature of the TPU extruder is set at 35 degrees Celsius. The extrusion head directs the heated material through the nozzle 120. During a nozzle preheating phase of printing preparation, the nozzle 120 may be wiped using a steel wire brush to clear any residue.

The nozzle 120 may be made of various materials, including, but not limited to brass or other materials adapted to deposit heated filament material. The nozzle 120 may further be sized to deposit the material. For example, the diameter of the nozzle 120 may be approximately 0.6 mm. The filament material may include various materials, such as TPE, and have a varying diameter. For example, the filament material is produced from a TPU extrusion filament at a diameter of approximately 3 mm. In one particular implementation, the printing profile includes a filament diameter set at 2.85 mm. The printing profile may further include an extrusion multiplier of approximately 1 and an extrusion width of approximately 0.85 mm.

The nozzle 120 deposits a first layer of the material at a first location on the bed 122. The fan assembly 116 and the bed 122 may be used to control a temperature of the deposited layers during thermal fusing. For example, the bed 122 may have a temperature set between approximately 35-40 degrees Celsius, and the fan speed may be set at 65. In one implementation, the printing profile sets a primary layer height, for example approximately 0.15 mm. A height and a width of the first layer may each be set at 100%. The printing profile further specifies other layer settings, such as top solid layers (e.g., 0), bottom solid layers (e.g., 0), an outline/perimeter shells (e.g., 1), an outline direction (e.g., inside-out), and/or the like. In one implementation, a fill angle is set to 0 degrees, which is parallel to a movement of the bed 122 in the y-axis.

The printing profile may further set printing speed. In one implementation, a default printing speed is set at approximately 2400 mm/min (40 mm/s). An outline (outer perimeter) underspeed and a first layer speed may also be set. For example, the first layer speed may be set at approximately 50%, and the outline underspeed may be set at approximately 80%. Further, a solid infill configuration may be provided to provide a complete lamination between distribution path lines. In one implementation, a solid infill underspeed is set to the same speed as the outline underspeed. The printing profile may include infill parameters, including, but not limited to, an internal fill pattern (e.g., rectilinear), an external infill pattern (e.g., rectilinear), an interior fill percentage (e.g., 100%), an outline overlap (e.g., 15%), an infill extrusion width (e.g., 200%), a solid diaphragm (e.g., every 1 layer), and infill angle offsets (e.g., 0 degrees).

After the first layer is deposited and thermally fused, the nozzle 120 moves relative to the bed 122 to deposit a second layer on top of or otherwise relative to the first layer or to change direction for depositing the second layer. Subsequent layers are deposited and thermally fused until customized polymeric cardiovascular medical device 102 is fabricated. The nozzle 120 may move in various directions (e.g., along an x, y, and/or z axis) relative to the bed 122 to fabricate the customized polymeric cardiovascular medical device 102 according to the print instructions. In some cases, the bed 122 may move relative the nozzle 120.

In one implementation, the nozzle 120 is leveled with respect to the bed 122 before each round of layer deposition to accommodate for the movement associated with manufacturing. Further, to account for variations in a distance of the nozzle 120 from the bed 122, a skirt may be printed with at least 10 mm of distance between the layer and the skirt, with a skirt outlines set at 2. These skirt/brim parameters may be set in the printing profile. To fine-tune the distance of the nozzle 120 to the bed 122, test samples may be printed and stopped prematurely to measure a thickness of the layer at a various locations and the distance adjusted accordingly.

The controller 114 causes the nozzle 120 to selectively deposit semi-molten filament material onto the bed 122 at coordinate positions specified by the print instructions. In one implementation, the controller 114 causes the nozzle 120 to coast at the end of the deposition of a layer to minimize variance in a thickness of the layers as the nozzle 120 changes directions. Stated differently, the coasting of the nozzle 120 as the nozzle 120 transitions from one deposition pass to another ceases extrusion of the filament material throughout the change of direction by the nozzle 120, thereby dissipating any built-up back pressure before a consistent velocity of the nozzle 120 resumes. As such, material buildup near approximately 180 degree direction changes from path to path were prevented, and approximately 30 mm of filament material was manually extruded before initiating manufacturing to eliminate any previous material and to buildup pressure in the nozzle 120.

After printing, the customized polymeric cardiovascular medical device 102 or a sheet of material from which to form the customized polymeric cardiovascular medical device 102 is peeled off the glass surface of the bed 122 and inspected for any potential defects.

As discussed herein, the print assembly 124 may alternatively use light to cure a photopolymer. In one implementation, the print assembly 124 includes a cartridge, roller, laser, and bed. The cartridge deposits drops of a liquid polymer, such as a photopolymer, onto the bed, which are hardened into a solid through exposure to light, such as ultraviolet (UV) light, generated by the laser. The print assembly 124 continues this process until the customized polymeric cardiovascular medical device 102 is complete. Alternatively or additionally, the print assembly 124 may perform a laser sintering process, such as Selective laser sintering (SLS), involving melting and fusing particles together to deposit successive cross-sections of the customized polymeric cardiovascular medical device 102. For example, the print assembly 124 may melt a flame-retardant plastic powder provided by the cartridge using the laser. The melted powder is then solidified to form a layer. The print assembly 124 continues this process until the customized polymeric cardiovascular medical device 102 is complete.

Figure 2:
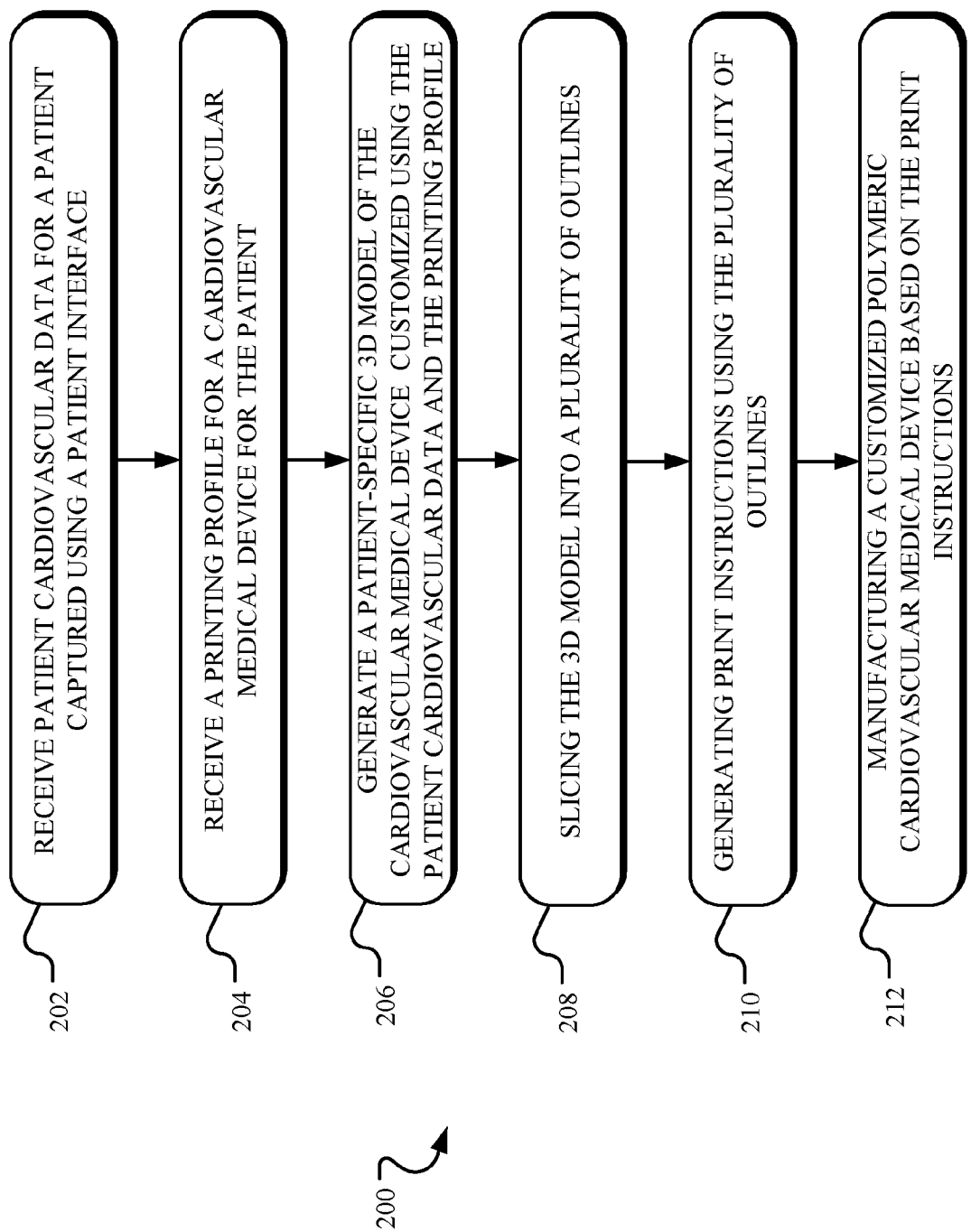
FIG. 2 is a flow chart illustrating example operations for manufacturing a customized polymeric cardiovascular device.

Referring to FIG. 2, a flow chart illustrating example operations 200 for manufacturing a customized polymeric cardiovascular medical device is shown. In one implementation, an operation 202 receives patient cardiovascular data for a patient at a controller. The patient cardiovascular data is captured using a patient interface.

An operation 204 receives a printing profile for a cardiovascular medical device at the controller. The printing profile may include a filament diameter, a temperature, a printing speed, a layer height, and/or a coasting distance. In one implementation, the printing profile is received from a user device or other interface with which a user inputs the printing profile. One or more parameters of the printing profile may be predefined. For example, the printing profile may be predefined based on a selection of a type of cardiovascular medical device and/or preferences of the surgeon that will implant the cardiovascular medical device.

An operation 206 generates a patient specific 3D model of the cardiovascular medical device customized for the patient using the patient cardiovascular data and the printing profile. In one implementation, the patient specific 3D model is generated using the controller. In another implementation, the patient specific 3D model is generated using the user device. An operation 208 slices the patient specific 3D model of the cardiovascular medical device into a plurality of outlines using the controller. The plurality of outlines may be sequential cross-sections of the patient specific 3D model. An operation 210 generates print instructions based on the plurality of outlines using the controller. The print instructions may be GCODE or another format defining actions of an printer assembly and other components of a 3D printer.

An operation 212 manufactures a customized polymeric cardiovascular medical device for the patient by manipulating a polymeric material according to the print instructions. In one implementation, the operation 212 deposits layers of thermoplastic elastomeric material, such as a thermoplastic polyurethane, according to the print instructions. In another implementation, the operation 212 exposes liquid polymeric material to a beam of light generated by a laser to harden the polymeric material. The customized polymeric cardiovascular medical device may be, for example, a heart valve, a surrogate blood vessel, a stent, and/or other surrogate tissue or biomaterial formulations. The customized polymeric cardiovascular medical device is manufactured for the patient and may include at least one micro-geometry or profile customized for the patient and/or the surgeon implanting the customized polymeric cardiovascular medical device. For example, the customized polymeric cardiovascular medical device may be a heart valve with customized leaflets. The micro-geometry may include, without limitation, one or more customized suture tabs, a customized flow manager, a customized vortex generator, and/or the like. Other aspects of the customized polymeric cardiovascular medical device may be customized for the patient, the surgeon, and/or the procedure. For example, the material of the customized polymeric cardiovascular medical device may include a customized flexibility, which may vary in different portions.

For examples of various customized polymeric cardiovascular medical devices 102, reference is made to FIGS. 3-10C. It will be appreciated that these depictions are exemplary only and not intended to be limiting. Other types of devices, micro-geometries, profiles, and the like are contemplated.

Figure 3:
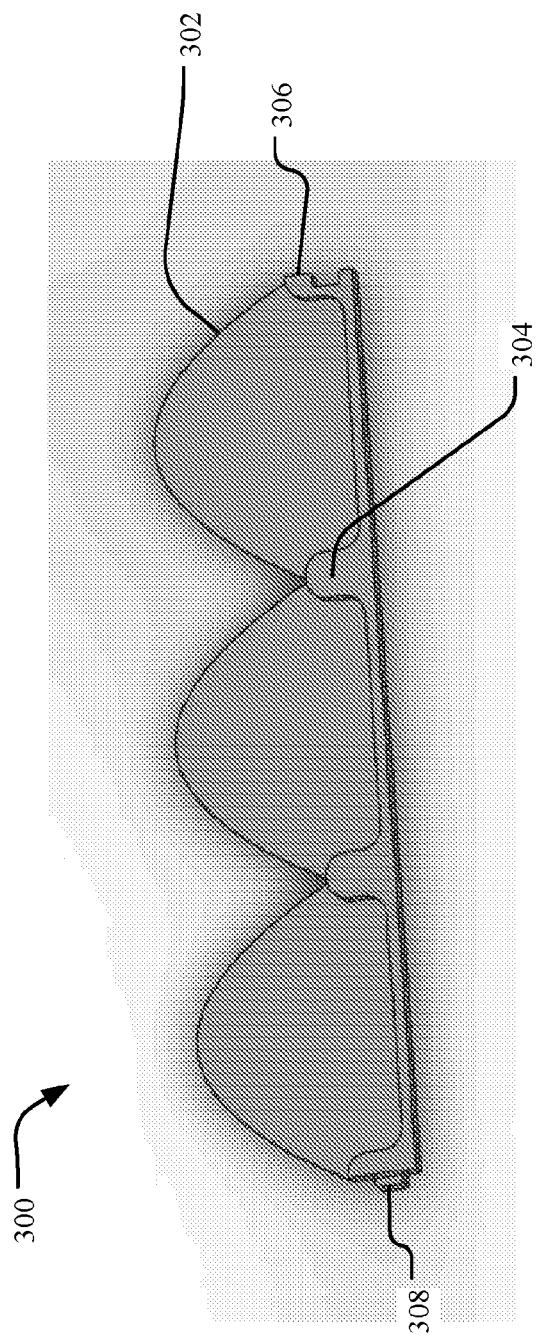
FIG. 3 illustrates an example heart valve leaflet sheet for a customized polymeric cardiovascular device.
Figure 7A:
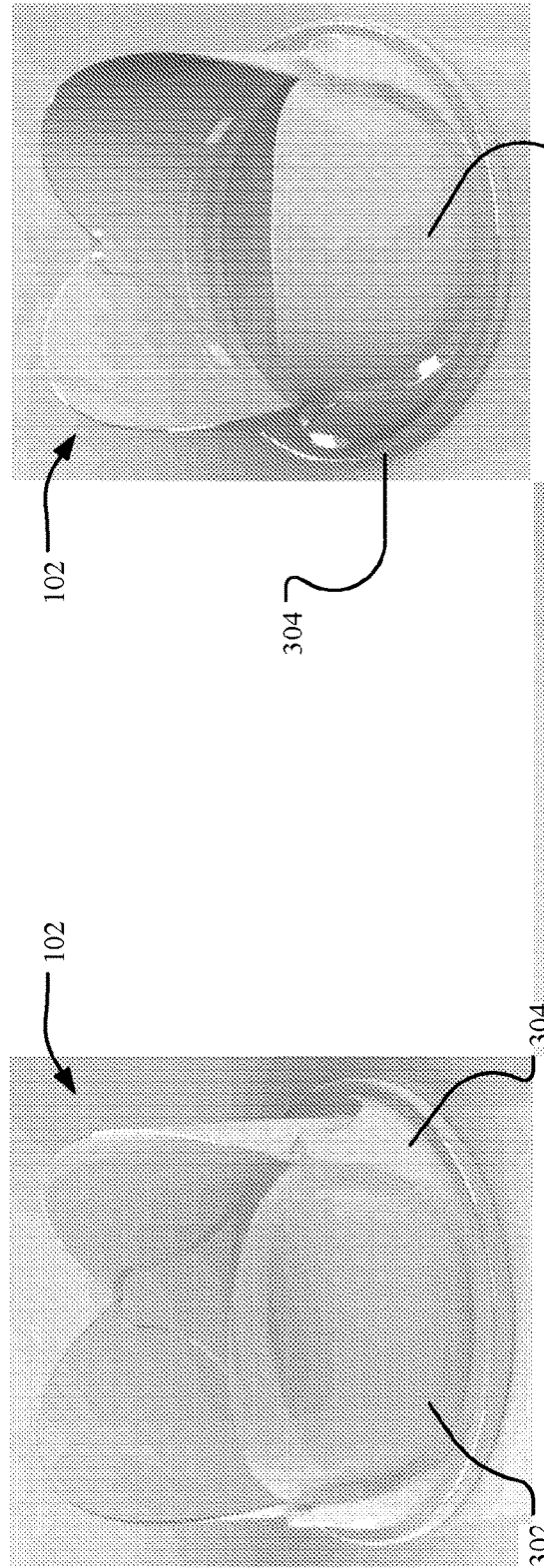
FIGS. 7A-7C are different perspective views of another heart valve with a taller leaflet profile.
Figure 7B:
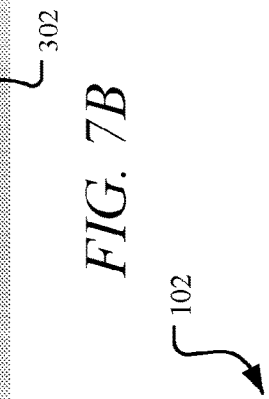
Figure 7C:
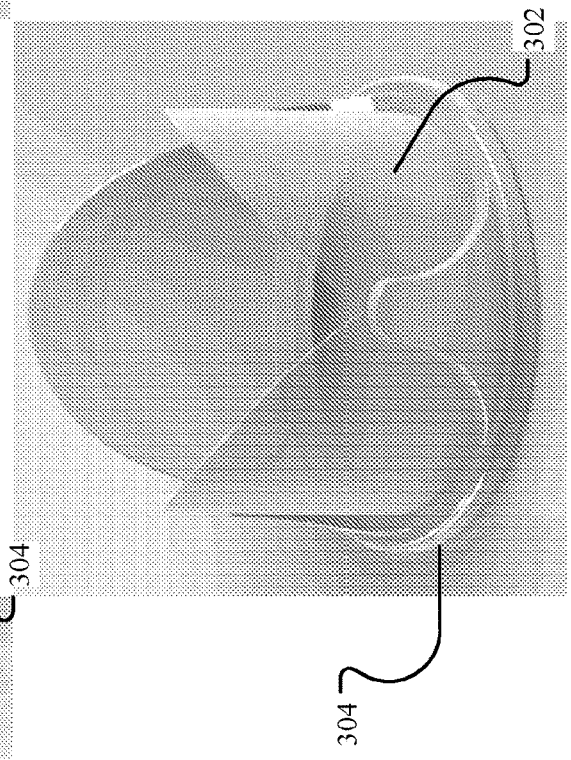

Turning first to FIG. 3, an example heart valve leaflet sheet 300 is shown. The heart valve leaflet sheet 300 is cut from a thin sheet of thermoplastic elastomeric material printed using the 3D printer 104, as described herein.

In one implementation, the heart valve leaflet sheet 300 includes valvular structures cut from the thin sheet of thermoplastic elastomeric material, including leaflets 302 and an annulus 304 extending between a proximal end 306 and a distal end 308. The number of leaflets 302 may vary depending on the target anatomy. For example, where the target anatomy is the pulmonary valve of the patient, the heart valve leaflet sheet 300 may have left, right, and anterior leaflets 302; where the target anatomy is the aortic valve of the patient, the heart valve leaflet sheet 300 may have left, right, and posterior leaflets 302; where the target anatomy is the tricuspid valve of the patient, the heart valve leaflet sheet 300 may have anterior, posterior, and septal leaflets 302; and where the target anatomy is the mitral valve of the patient, the heart valve leaflet sheet 300 may have anterior and posterior leaflets 302.

To create the customized polymeric cardiovascular medical devices 102 in the form of a functioning heart valve, the annulus 304 may be wrapped around a rod or similar device and the proximal end 306 engaged to the distal end 308. Alternatively, the customized polymeric cardiovascular medical devices 102 may be printed directly into the overall geometry of a functioning heart valve without the annulus being wrapped around a rod. The proximal end 306 may include a channel configured to receive a projection of the distal end 308. Once the proximal end 306 and the distal end 308 are engaged, the annulus 304 forms a ring with the leaflets 302 extending in a direction away from the annulus 304. The annulus 304 may further include a tab disposed at each point at which adjacent leaflets 302 meet. The tabs extend in the same direction away from the annulus 304 as the leaflets 302.

The leaflets 304 provide occluding surfaces that during use are pushed open to allow blood flow and then closed together to seal and prevent back flow. As described herein, the heart valve leaflet sheet 300 may include various features customized for the patient and be sized and shaped to match the target anatomy of the patient. In one implementation, the heart valve leaflet sheet 300 includes one or more surfaces adapted to compensate for a malformity in the target anatomy of the patient. For example, the patient may have a malformity in the aortic wall, and the heart valve leaflet sheet 300 may include one or more surfaces or other features adapted to compensate for the malformity to restore the heart valve to a baseline functionality.

Alternatively or additionally, the heart valve leaflet sheet 300 may include one or more micro-geometries customized for the patient, the medical professional, and/or the procedure. For example, the micro-geometries may include customized flow manager geometries adapted to manage vortex generation and flow for the patient, as well as reduce damage to blood cells that could result in clotting. Examples of such flow manager geometries are illustrated in FIGS. 4A-5D.

Referring to FIG. 4A, in one implementation, the customized flow manager geometry includes a set of elongated tread protrusions 310. Each of the elongated tread protrusions 310 is disposed on a surface of one of the leaflets 302. In one implementation, each of the elongated tread protrusions 310 extends along a curve mirroring a shape of an edge of the leaflet 302. As shown in FIG. 4B, the customized flow manager geometry may further include a second set of elongated tread protrusions 312 disposed on the surface of the leaflets 302 relative to the set of elongated tread protrusions 310. These micro-geometries may be used, for example, to facilitate a complete closure of the leaflets 302.

In another implementation illustrated in FIG. 4C, the customized flow manager geometry includes a set of broken tread protrusions 316. Each of the sets of broken tread protrusions 316 may include a plurality of tread protrusions disposed on a surface of one of the leaflets 302 and separated from each other by a gap. For example, each of the sets of broken tread protrusions 316 may include a central tread protrusion separated from a first side tread protrusion and a second side tread protrusion by a first gap and a second gap, respectively. The broken tread protrusions 316 may be disposed along a curve mirroring a shape of an edge of the leaflet 302.

Turning next to FIGS. 4D-5B, the customized flow manager geometry may include a tread grid disposed on each of the leaflets 302. The tread grid may include any number of treads arranged in various patterns. Further, the treads in the tread grid may be a variety of shapes and sizes and may be in the form of protrusions, indentations, grooves, and/or the like. For example, the tread grid may include a plurality of circular protrusions 314 extending from each of the surfaces of the leaflets 302 as shown in FIG. 4D. In another example shown in FIG. 5A, the tread grid may include a plurality of tear-drop protrusions 318 defined on each of the surfaces of the leaflets 302. In yet another example shown in FIG. 5B, the tread grid may include a plurality of angled protrusions 320 forming a V-shape defined on each of the surfaces of the leaflets 302.

FIG. 5C illustrates the customized flow manager geometry in the form of a set of grooves 320 defined each of the surfaces of the leaflets 302. In one implementation, the set of grooves 322 includes a first groove extending along a curve from a first location on an edge of the leaflet 302 to a second location on the edge of the leaflet. The curve may extend from the first location in a direction towards the annulus 304 and back to the second location. The set of grooves 322 may include one or more additional grooves extending parallel to the first groove.

Referring to FIG. 5D, the customized flow manager geometry may include a channel 324 extending through each of the surfaces of the leaflets 302. In one implementation, each of the channels 324 extends along one or more curves.

FIGS. 6A-8C illustrate the customized polymeric cardiovascular medical device 102 in the form a heart valve. FIGS. 6A and 6B show an example heart valve with the leaflets 302 folded and FIGS. 7A-7C show another example heart valve with the leaflets displaced. It will be understood from FIGS. 6A-7C that the heart valve leaflet sheet 300 may include a customized size, shape, and/or profile of one or more surfaces or features. In one implementation, the leaflets 302 have a customized profile. For example, as shown in FIGS. 7A-7C, the leaflets 302 may have a tall profile with the surfaces of the leaflets 302 having an extended length away from the annulus 304. The leaflets 302 shown in FIGS. 8B-8C have a relatively shorter profile compared to the leaflets 302 shown in FIGS. 7A-7C.

As further shown in FIGS. 8A-8C, the micro-geometries may be customized for the medical professional and/or the procedure. For example, the micro-geometries may include, without limitation, one or more suture tabs, suture holes, implantation indentations, and/or the like. FIGS. 8A-8C each illustrate a set of suture holes 326 defined in a surface of the annulus 304. The suture holes 326 may extend through the surface of the annulus 304 in a direction parallel to the leaflets 302, in a direction towards a center of the annulus 304, and/or at an angle relative to the leaflets 302. In one implementation, the sets of suture holes 326 may be spaced evenly from each other around the annulus 304. Each set of suture holes 326 may include one or more suture holes 326. Further, the suture holes 326 within each set may be evenly spaced from each other or grouped. For example, each set may include a center suture hole 326 spaced closer to a first adjacent suture hole 326 than a second adjacent suture hole 326, as shown in FIG. 8A.

Figure 9B:
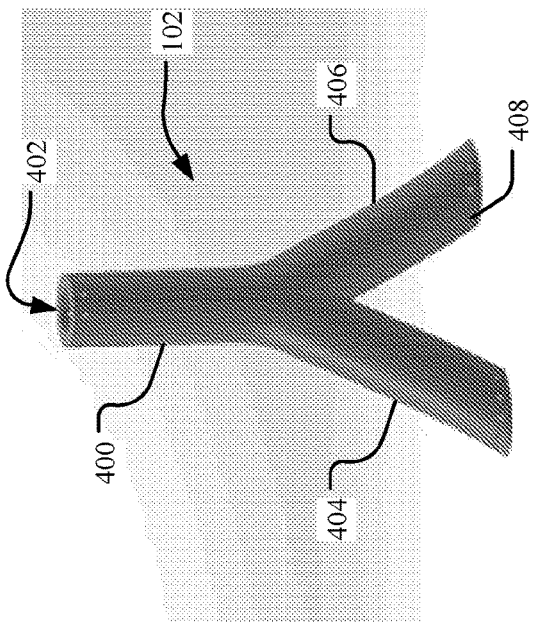
FIG. 9B shows the surrogate blood vessel with customized suture holes.
Figure 9C:
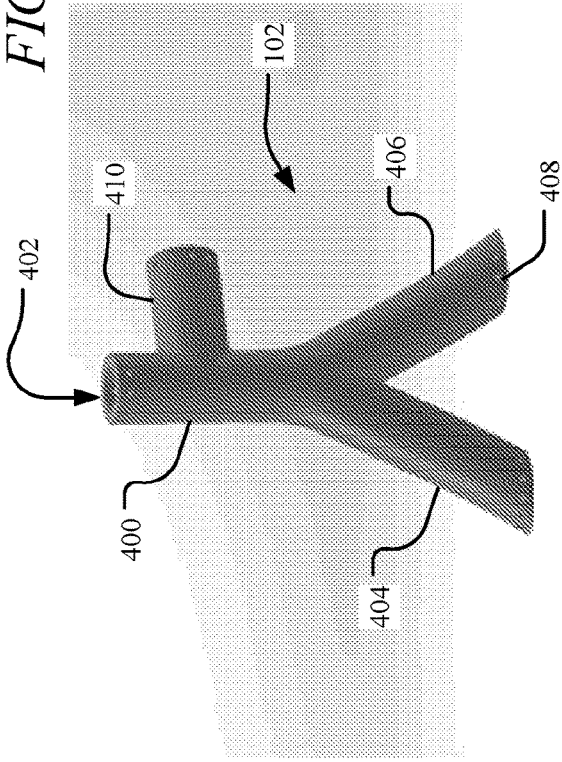
FIG. 9C shows the surrogate blood vessel with a renal artery surrogate bifurcating from the descending aortic surrogate segment.
Figure 9A:
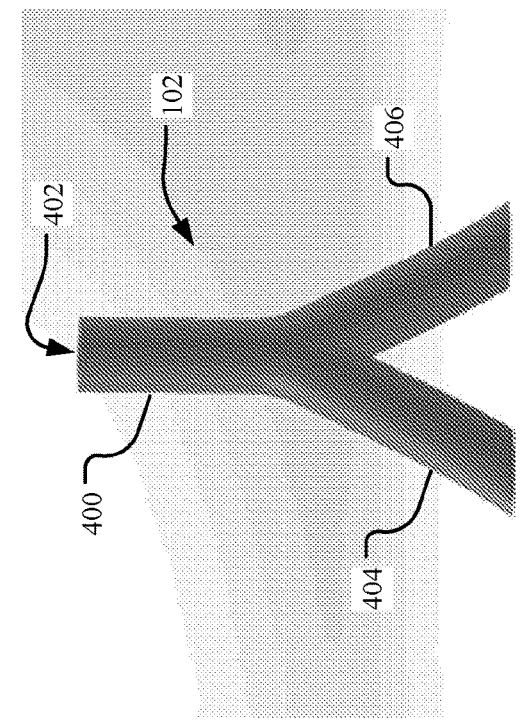
FIG. 9A illustrates another example customized polymeric cardiovascular device in the form of a surrogate blood vessel.

For examples of various customized polymeric cardiovascular medical devices 102 in the form of a surrogate blood vessel, such as a vascular graft, reference is made to FIGS. 9A-9C. It will be appreciated that surrogate blood vessels of any configuration customized for the patient may be manufactured as described herein. The surrogate blood vessel may include one or more patient-specific shapes and match the morphology of the target anatomy of the patient as well as the physician preferences for installation.

For example, as shown in FIGS. 9A-9C, the customized polymeric cardiovascular medical device 102 in the form of a surrogate blood vessel may include a descending aortic surrogate 400 and radial artery surrogates (e.g., 404 and 406) forking from the descending aortic surrogate 400. A renal artery surrogate 410 may bifurcate from the descending aortic surrogate 400. These configurations may be used to manage vortex generation, manage flow, and/or the like while compensating for patient-specific idiosyncrasies. Additionally or alternatively, one or more portions of the surrogate blood vessel may include a customized flexibility (e.g., an increased flexibility, an enhanced strength, thickness, etc.).

The surrogate blood vessel may further include one or more micro-geometries customized for the patient (e.g., to further manage vortex generation and/or flow and minimize damage to blood vessels), the physician, and/or the procedure. In one implementation, the surrogate blood vessel includes a micro-geometry in the form of one or more suture holes 408 customized for the physician. The suture holes 408 may extend through a wall of the descending aortic surrogate 400 and the radial artery surrogates 404 and 406, and/or the renal artery surrogate 410. Additional micro-geometries customized for the physician or procedure may include, without limitation, implant indentations, patterns, and the like. Further, the overall geometry and micro-geometries may take a variety of different shapes and sizes with different features to accommodate trauma cases.

Figure 10C:
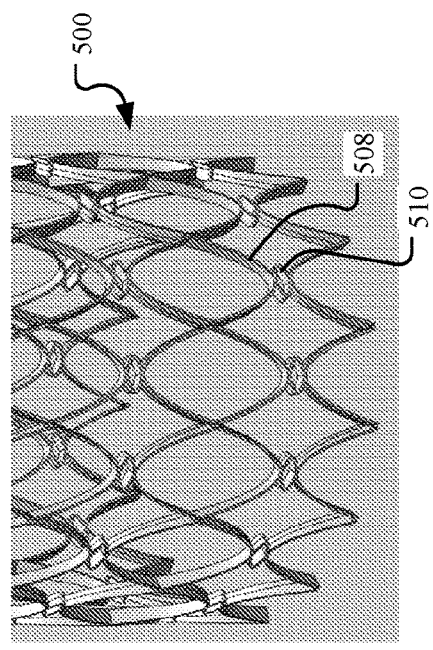
FIGS. 10A-10C illustrate side, proximal perspective, and detailed distal views, respectively, of another example customized polymeric cardiovascular device in the form of a stent.
Figure 10B:
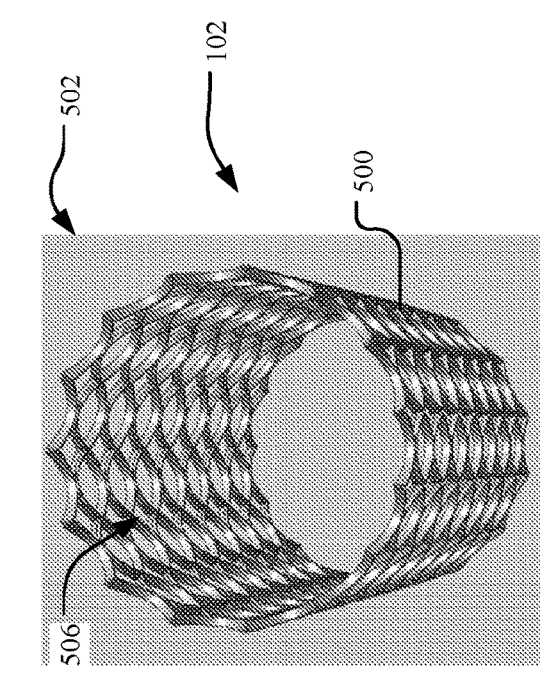
Figure 10A:
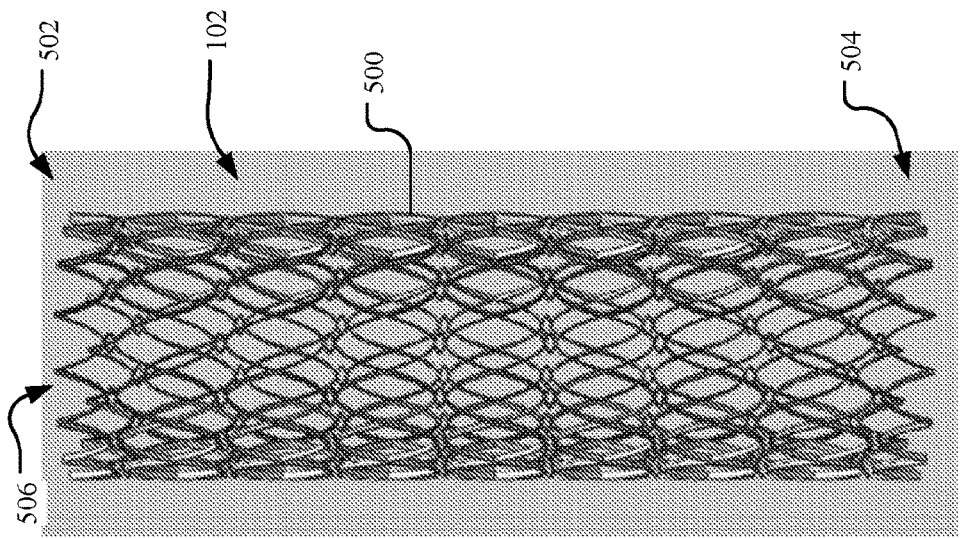

For an example customized polymeric cardiovascular medical devices 102 in the form of a stent, reference is made to FIGS. 10A-10C, which show side, proximal perspective, and detailed distal views, respectively, of the stent.

In one implementation, the stent includes a mesh body 500 extending between a proximal end 502 and a distal end 504. An opening 506 extends through the mesh body 506. The mesh body 500 may include one or more customized stent segments, such as struts, connecting members, ends, and/or the like fabricating a micro-geometry in the form of a customized contiguous mesh pattern for the patient. In the example shown in FIGS. 10A-10C, the mesh body 500 includes a micro-geometry having customized stent segments 508 and 510 that collectively form a customized contiguous mesh pattern.

The mesh body 500 may further have an overall shape customized to perform within the target anatomy of the patient, such as an artery. For example, the mesh body may have a cylindrical shape. In addition to the mesh pattern and overall shape of the mesh body 500 being customizable, other aspects of the mesh body 500 may be customizable for the patient, including, but not limited to, a thickness of the material of the mesh body 500, a flexibility of one or more portions of the mesh body 500, a size of the mesh body 500, and/or the like.

Figure 11:
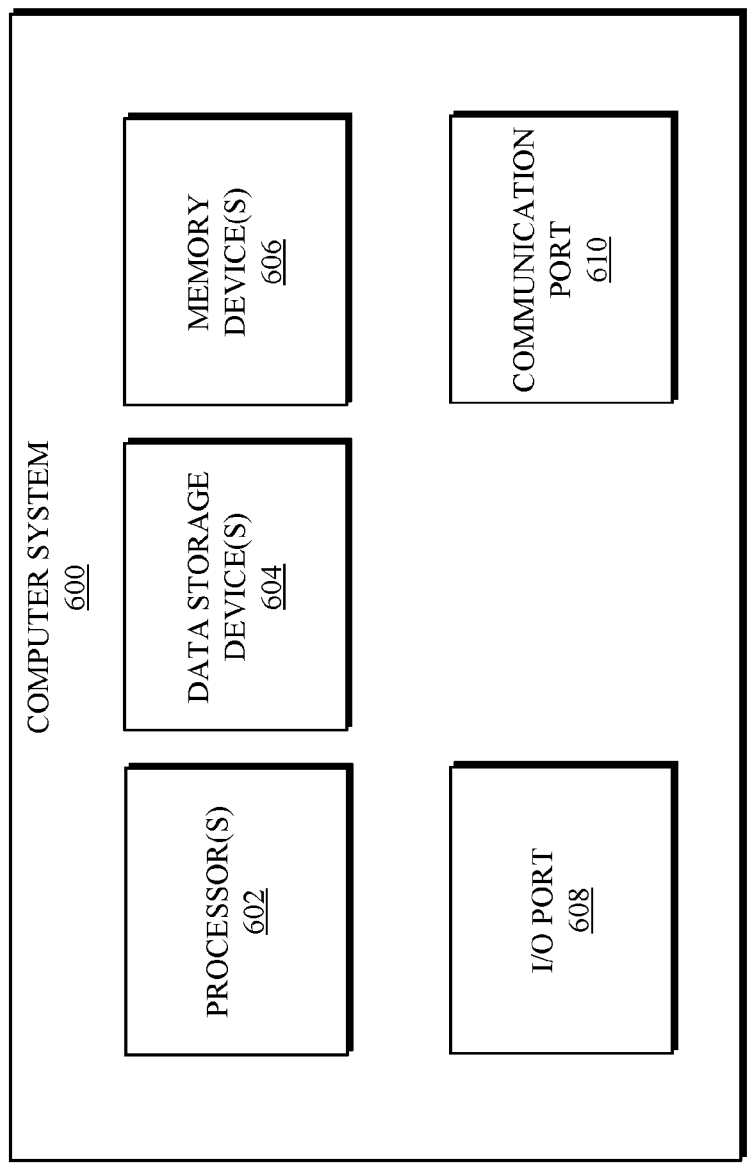
FIG. 11 is an example computing system that may implement various systems and methods discussed herein.

Referring to FIG. 11, a detailed description of an example computing system 1100 having one or more computing units that may implement various systems and methods discussed herein is provided. The computing system 1100 may be applicable to the patient interface, the controller, the extruder assembly, the user device, and other computing or network devices. It will be appreciated that specific implementations of these devices may be of differing possible specific computing architectures not all of which are specifically discussed herein but will be understood by those of ordinary skill in the art.

The computer system 1100 may be a computing system is capable of executing a computer program product to execute a computer process. Data and program files may be input to the computer system 1100, which reads the files and executes the programs therein. Some of the elements of the computer system 1100 are shown in FIG. 11, including one or more hardware processors 1102, one or more data storage devices 1104, one or more memory devices 1108, and/or one or more ports 1108-1310. Additionally, other elements that will be recognized by those skilled in the art may be included in the computing system 1100 but are not explicitly depicted in FIG. 11 or discussed further herein. Various elements of the computer system 1100 may communicate with one another by way of one or more communication buses, point-to-point communication paths, or other communication means not explicitly depicted in FIG. 11.

The processor 1102 may include, for example, a central processing unit (CPU), a microprocessor, a microcontroller, a digital signal processor (DSP), and/or one or more internal levels of cache. There may be one or more processors 1102, such that the processor 1102 comprises a single central-processing unit, or a plurality of processing units capable of executing instructions and performing operations in parallel with each other, commonly referred to as a parallel processing environment.

The computer system 1100 may be a conventional computer, a distributed computer, or any other type of computer, such as one or more external computers made available via a cloud computing architecture. The presently described technology is optionally implemented in software stored on the data stored device(s) 1104, stored on the memory device (s) 1106, and/or communicated via one or more of the ports 1108-1310, thereby transforming the computer system 1100 in FIG. 11 to a special purpose machine for implementing the operations described herein. Examples of the computer system 1100 include personal computers, terminals, workstations, mobile phones, tablets, laptops, personal computers, multimedia consoles, gaming consoles, set top boxes, and the like.

The one or more data storage devices 1104 may include any non-volatile data storage device capable of storing data generated or employed within the computing system 1100, such as computer executable instructions for performing a computer process, which may include instructions of both application programs and an operating system (OS) that manages the various components of the computing system 1100. The data storage devices 1104 may include, without limitation, magnetic disk drives, optical disk drives, solid state drives (SSDs), flash drives, and the like. The data storage devices 1104 may include removable data storage media, non-removable data storage media, and/or external storage devices made available via a wired or wireless network architecture with such computer program products, including one or more database management products, web server products, application server products, and/or other additional software components. Examples of removable data storage media include Compact Disc Read-Only Memory (CD-ROM), Digital Versatile Disc Read-Only Memory (DVD-ROM), magneto-optical disks, flash drives, and the like. Examples of non-removable data storage media include internal magnetic hard disks, SSDs, and the like. The one or more memory devices 1106 may include volatile memory (e.g., dynamic random access memory (DRAM), static random access memory (SRAM), etc.) and/or non-volatile memory (e.g., read-only memory (ROM), flash memory, etc.).

Computer program products containing mechanisms to effectuate the systems and methods in accordance with the presently described technology may reside in the data storage devices 1104 and/or the memory devices 1106, which may be referred to as machine-readable media. It will be appreciated that machine-readable media may include any tangible non-transitory medium that is capable of storing or encoding instructions to perform any one or more of the operations of the present disclosure for execution by a machine or that is capable of storing or encoding data structures and/or modules utilized by or associated with such instructions. Machine-readable media may include a single medium or multiple media (e.g., a centralized or distributed database, and/or associated caches and servers) that store the one or more executable instructions or data structures.

In some implementations, the computer system 1100 includes one or more ports, such as an input/output (I/O) port 1108 and a communication port 1110, for communicating with other computing, network, or vehicle devices. It will be appreciated that the ports 1108-1310 may be combined or separate and that more or fewer ports may be included in the computer system 1100.

The I/O port 1108 may be connected to an I/O device, or other device, by which information is input to or output from the computing system 1100. Such I/O devices may include, without limitation, one or more input devices, output devices, and/or environment transducer devices.

In one implementation, the input devices convert a human-generated signal, such as, human voice, physical movement, physical touch or pressure, and/or the like, into electrical signals as input data into the computing system 1100 via the I/O port 1108. Similarly, the output devices may convert electrical signals received from computing system 1100 via the I/O port 1108 into signals that may be sensed as output by a human, such as sound, light, and/or touch. The input device may be an alphanumeric input device, including alphanumeric and other keys for communicating information and/or command selections to the processor 1102 via the I/O port 1108. The input device may be another type of user input device including, but not limited to: direction and selection control devices, such as a mouse, a trackball, cursor direction keys, a joystick, and/or a wheel; one or more sensors, such as a camera, a microphone, a positional sensor, an orientation sensor, a gravitational sensor, an inertial sensor, and/or an accelerometer; and/or a touch-sensitive display screen ("touchscreen"). The output devices may include, without limitation, a display, a touchscreen, a speaker, a tactile and/or haptic output device, and/or the like. In some implementations, the input device and the output device may be the same device, for example, in the case of a touchscreen.

The environment transducer devices convert one form of energy or signal into another for input into or output from the computing system 1100 via the I/O port 1108. For example, an electrical signal generated within the computing system 1100 may be converted to another type of signal, and/or vice-versa. In one implementation, the environment transducer devices sense characteristics or aspects of an environment local to or remote from the computing device 1100, such as, light, sound, temperature, pressure, magnetic field, electric field, chemical properties, physical movement, orientation, acceleration, gravity, and/or the like. Further, the environment transducer devices may generate signals to impose some effect on the environment either local to or remote from the example computing device 1100, such as, physical movement of some object (e.g., a mechanical actuator), heating or cooling of a substance, adding a chemical substance, and/or the like.

In one implementation, a communication port 1110 is connected to a network by way of which the computer system 1100 may receive network data useful in executing the methods and systems set out herein as well as transmitting information and network configuration changes determined thereby. Stated differently, the communication port 1110 connects the computer system 1100 to one or more communication interface devices configured to transmit and/or receive information between the computing system 1100 and other devices by way of one or more wired or wireless communication networks or connections. Examples of such networks or connections include, without limitation, Universal Serial Bus (USB), Ethernet, Wi-Fi, Bluetooth®, Near Field Communication (NFC), Long-Term Evolution (LTE), and so on. One or more such communication interface devices may be utilized via the communication port 1110 to communicate one or more other machines, either directly over a point-to-point communication path, over a wide area network (WAN) (e.g., the Internet), over a local area network (LAN), over a cellular (e.g., third generation (3G) or fourth generation (4G)) network, or over another communication means. Further, the communication port 1110 may communicate with an antenna or other link for electromagnetic signal transmission and/or reception.

In an example implementation, patient cardiovascular data, 3D models, print profiles, and software and other modules and services may be embodied by instructions stored on the data storage devices 1104 and/or the memory devices 1106 and executed by the processor 1102. The computer system 1100 may be integrated with or otherwise form part of the 3D printer 104.

The system set forth in FIG. 11 is but one possible example of a computer system that may employ or be configured in accordance with aspects of the present disclosure. It will be appreciated that other non-transitory tangible computer-readable storage media storing computer-executable instructions for implementing the presently disclosed technology on a computing system may be utilized.

In the present disclosure, the methods disclosed may be implemented as sets of instructions or software readable by a device. Further, it is understood that the specific order or hierarchy of steps in the methods disclosed are instances of example approaches. Based upon design preferences, it is understood that the specific order or hierarchy of steps in the method can be rearranged while remaining within the disclosed subject matter. The accompanying method claims present elements of the various steps in a sample order, and are not necessarily meant to be limited to the specific order or hierarchy presented.

The described disclosure may be provided as a computer program product, or software, that may include a non-transitory machine-readable medium having stored thereon instructions, which may be used to program a computer system (or other electronic devices) to perform a process according to the present disclosure. A machine-readable medium includes any mechanism for storing information in a form (e.g., software, processing application) readable by a machine (e.g., a computer). The machine-readable medium may include, but is not limited to, magnetic storage medium, optical storage medium; magneto-optical storage medium, read only memory (ROM); random access memory (RAM); erasable programmable memory (e.g., EPROM and EEPROM); flash memory; or other types of medium suitable for storing electronic instructions.

While the present disclosure has been described with reference to various implementations, it will be understood that these implementations are illustrative and that the scope of the present disclosure is not limited to them. Many variations, modifications, additions, and improvements are possible. More generally, embodiments in accordance with the present disclosure have been described in the context of particular implementations. Functionality may be separated or combined in blocks differently in various embodiments of the disclosure or described with different terminology. These and other variations, modifications, additions, and improvements may fall within the scope of the disclosure as defined in the claims that follow.

What is claimed is:

1. A manufacturing system comprising:
   a patient interface configured to capture patient cardiovascular data for a patient;
   a controller in communication with the patient interface, the controller configured to generate print instructions based on a plurality of outlines sliced from a patient specific three-dimensional model of a heart valve for the patient, the patient specific three-dimensional model of the heart valve customized for the patient using the patient cardiovascular data and a printing profile; and
   a print assembly in communication with the controller, the print assembly configured to manipulate layers of polymeric material according to the print instructions into a customized polymeric heart valve for the patient, the customized polymeric heart valve having an annulus and a plurality of customized leaflets extending from the annulus, one or more of the leaflets comprising a customized flow manager microgeometry, and wherein manipulating the layers of polymeric material includes depositing, layer by layer, the polymeric material to form the customized polymeric cardiovascular medical device heart valve using three-dimensional (3D) printing.

2. The manufacturing system of claim 1, wherein the print assembly includes an extruder assembly configured to deposit the layers of the polymeric material according to the print instructions.

3. The manufacturing system of claim 1, wherein the printing profile includes at least one of: a filament diameter; a temperature; a printing speed; a layer height; or a coasting distance.

4. The manufacturing system of claim 1, wherein the print assembly is configured to harden the layers of the polymeric material through exposure to light generated by a laser according to the print instructions.

5. The manufacturing system of claim 1, wherein the customized polymeric heart valve is formed with a sheet of thermoplastic elastomeric material, the customized polymeric heart valve configured to be separated from the sheet prior to implanting the customized polymeric heart valve into the patient.

6. The manufacturing system of claim 1, wherein the annulus includes a proximal end and a distal end configured to couple together prior to implanting the customized polymeric heart valve into the patient.

7. The manufacturing system of claim 1, wherein each of the plurality of customized leaflets is configured to transition between an open position and a closed position, each of the plurality of customized leaflets including an occluding surface configured to prevent backflow when each of the plurality of customized leaflets are in the closed position.

8. The manufacturing system of claim 1, wherein each of the plurality of customized leaflets are sized and shaped to match target anatomy of the patient, wherein the target anatomy includes at least one of a pulmonary valve of the patient, an aortic valve of the patient, a tricuspid valve of the patient, or a mitral valve of the patient.

9. The manufacturing system of claim 8, wherein the plurality of customized leaflets includes left, right, and anterior leaflets when the target anatomy is the pulmonary valve of the patient, wherein the plurality of customized leaflets includes left, right, and posterior leaflets when the target anatomy is the aortic valve of the patient, wherein the plurality of customized leaflets includes anterior, posterior, and septal leaflets when the target anatomy is the tricuspid valve of the patient, and wherein the plurality of customized leaflets includes anterior and posterior leaflets when the target anatomy is the mitral valve of the patient.

10. The manufacturing system of claim 1, wherein each of the plurality of customized leaflets includes a surface having a first elongated tread protrusion thereon.

11. The manufacturing system of claim 10, wherein each of the plurality of customized leaflets includes an edge, each first elongated tread protrusion defining a curve that corresponds to the edge.

12. The manufacturing system of claim 10, wherein the surface includes a second elongated tread protrusion thereon.

13. The manufacturing system of claim 1, wherein each of the plurality of customized leaflets includes a surface having a broken tread protrusion, each broken tread protrusion including a central tread protrusion, a first side tread protrusion separated from the central tread protrusion by a first gap, and a second side tread protrusion separated from the central tread protrusion by a second gap.

14. The manufacturing system of claim 1, wherein each of the plurality of customized leaflets includes a surface having a tread grid defined thereon, the tread grid including at least one of a plurality of circular protrusions, a plurality of tear-drop protrusions, or a plurality of V-shaped protrusions.

15. The manufacturing system of claim 1, wherein each of the plurality of customized leaflets includes a surface having a first groove extending along a curve and a second groove extending parallel to the first groove.

16. The manufacturing system of claim 1, wherein each of the plurality of customized leaflets includes a surface having a channel extending therethrough.

17. The manufacturing system of claim 1, wherein the annulus further comprises a plurality of suture holes extending therethrough.

18. The manufacturing system of claim 1, wherein the annulus further comprises one or more suture tabs.

19. The manufacturing system of claim 1, wherein the patient interface includes at least one of a probe, an electrocardiograph, an ultrasound device, a computed tomography device, a magnetic resonance imaging device, or a device for measuring or capturing the patient cardiovascular data.

20. The manufacturing system of claim 19, wherein the patient interface includes an ultrasonic transducer configured to produce and detect ultrasonic waves.

21. The manufacturing system of claim 1, wherein the customized flow manager micro-geometry is configured to manage vortex generation.

22. The manufacturing system of claim 1, wherein the customized flow manager micro-geometry is configured to reduce damage to blood cells.

* * * * *

UNITED STATES PATENT AND TRADEMARK OFFICE
CERTIFICATE OF CORRECTION

PATENT NO. : 11,957,572 B2
APPLICATION NO. : 16/475153
DATED : April 16, 2024
INVENTOR(S) : David Prawel Page 1 of 1

It is certified that error appears in the above-identified patent and that said Letters Patent is hereby corrected as shown below:

In the Claims

Claim 1, Column 14, Lines 47-48, delete "cardiovascular medical device".

Signed and Sealed this
Eleventh Day of March, 2025

Coke Morgan Stewart
*Acting Director of the United States Patent and Trademark Office*